Figure 13:
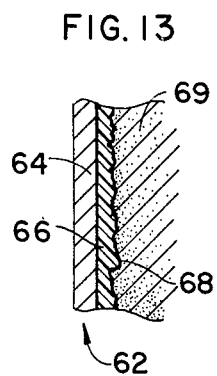

United States Patent [19]

McDonald et al.

[11] 4,250,035
[45] Feb. 10, 1981

[54] RADIAL COMPRESSION OF PACKED BEDS

[75] Inventors: Patrick D. McDonald, Holliston; Carl W. Rausch, Auburndale, both of Mass.

[73] Assignee: Waters Associates, Inc., Milford, Mass.

[21] Appl. No.: 960,606

[22] Filed: Nov. 13, 1978

Related U.S. Application Data

[63] Continuation of Ser. No. 848,752, Nov. 4, 1977, abandoned, which is a continuation of Ser. No. 638,301, Dec. 8, 1975, abandoned.

[51] Int. Cl.³ .............................................. B01D 15/08
[52] U.S. Cl. .................................. 210/198.2; 55/386; 206/305; 206/528; 210/351
[58] Field of Search ............... 210/31 C, 198 C, 350, 210/351; 55/67, 197, 386, 475, 390; 206/521, 522, 528, 530, 305

[56] References Cited

U.S. PATENT DOCUMENTS

| 3,017,996 | 1/1962 | Riley | 210/351 X |
| 3,180,825 | 4/1965 | Covreur et al. | 210/351 X |
| 3,266,628 | 8/1966 | Price | 55/475 X |
| 3,349,920 | 10/1967 | Waters | 210/198 C |
| 3,487,938 | 1/1970 | Patterson | 210/198 C |
| 3,791,522 | 2/1974 | Eisenbeiss | 210/198 C |
| 3,966,609 | 6/1976 | Godbille et al. | 210/198 C |

OTHER PUBLICATIONS

CHRO Max Bulletin-Ivan Sorvales Inc., Norwalk, Conn. 34/99.

Primary Examiner—John Adee

[57] ABSTRACT

Improved liquid chromatographic apparatus and an improved process for making and utilizing a chromatographic column. By providing means to exert radial pressure on the column packing, the packing efficiency of the column is increased and is more reproducible, and greater uniformity can be achieved in column performance both among packed columns of the same kind and during the useful life of a given packed column.

41 Claims, 16 Drawing Figures

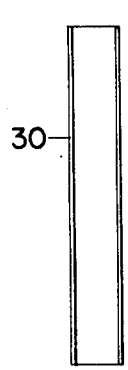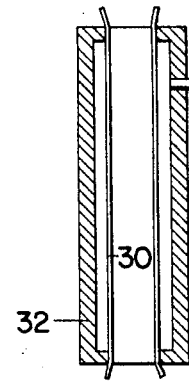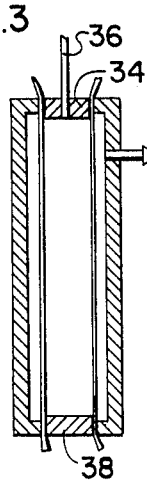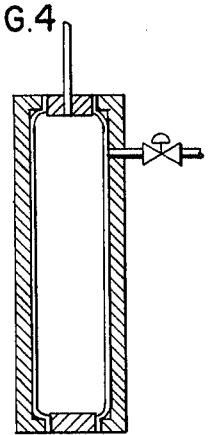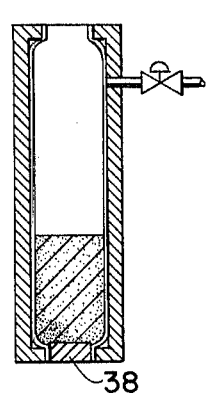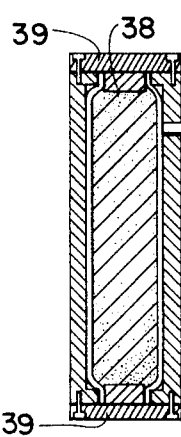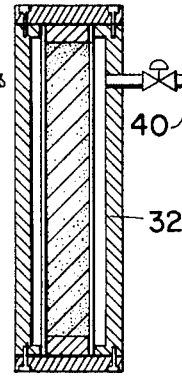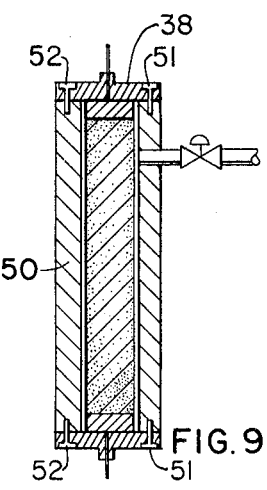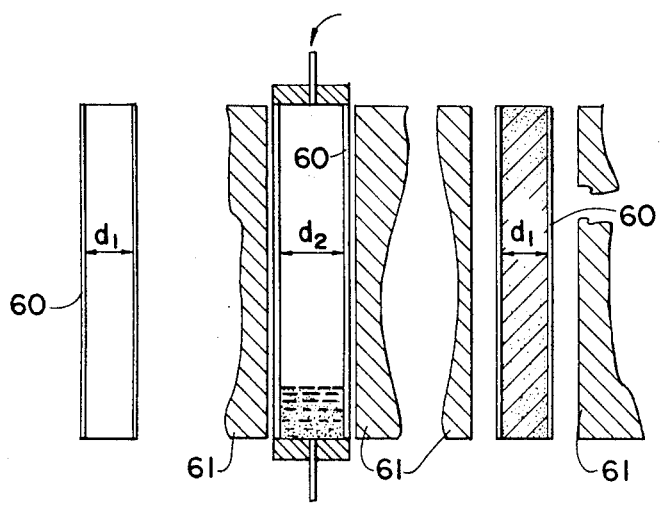

RADIAL COMPRESSION OF PACKED BEDS

This is a continuation of application Ser. No. 848,752, filed Nov. 4, 1977, now abandoned which in turn is a continuation of application Ser. No. 638,301, filed Dec. 8, 1975 abandoned.

BACKGROUND OF THE INVENTION

Liquid chromatography is a process utilized in both preparative and analytical chemistry. Essentially, the process comprises a stationary phase interacting with a mobile phase. Typically, the stationary phase is a surface-active powder such as silica, alumina, or an inert size-separating material like a gel-permeation chromatography packing, or the like. This powder is contained in a chromatographic column. A mobile phase, generally consisting of a carrier fluid and a sample of a chemical to be identified, analyzed, or purified, is passed through the column. A typical utility of the process is to identify various chemical components in an unknown sample. This identification is made by (1) using an immobile phase which differentially retards the progress of different components of the sample through the column so that the components are separated and leave the column at different times and (2) continuously analyzing the effluent of the column over a period of time. The separation is achieved when one component of the sample has more affinity for the stationary phase than does another component. Also, the separation may be achieved by an exclusion process based on the difference in sizes between molecules, e.g. by gel-permeation chromatography processes. The invention to be described below is related to achieving better and more dependable identity of the sample components by improving the efficiency of the process in such a way as to provide better resolution of the sample.

In order to achieve separation of sample components which are very close to each other in chemical and physical properties, highly sophisticated procedures have been developed in the many processing techniques associated with liquid chromatography. Special pumps and valves have been developed for presenting samples to the inlet of the chromatographic columns with as much integrity as is possible to avoid building into the process an initial and inherent dispersal of the sample which dispersal would tend to reduce the resolution capabilities of the chromatographic packing within the column. Moreover, much work has been done to provide flow-distributing devices at the inlet of the column to assure the even placement of the sample across the columns cross-sectional area. Also, a great deal of technical effort has provided improved chromatographic packings and highly-sophisticated analytical apparatus for measuring various properties of the liquid effluent leaving the column.

Despite such work as has been described above, it has remained a problem to achieve an uniform packing of the chromatographic material into a column. Many techniques have been suggested including vibration (See U.S. Pat. No. 3,300,849): All of these techniques require careful control if segregation of particles by size is to be avoided and uniformly packed columns are to be obtained. Even after the column is filled, problems exist in maintaining the filling in proper condition during transportation and operation of the packed columns. (See U.S. Pat. No. 3,349,920 to Waters.)

In general, the most commonly used practice of filling a high-performance column has been a costly method including slurrying the packing and passing the slurry into the column; thereby, in effect, using the column itself as a form for placing a "filter cake" of chromatographic packing therein. Each this costly, time-consuming method of column manufacture is not without problems caused by shifting of the packing during shipment when it can be subjected to various vibration and other transient, non-predictable physical abuse. This tends to cause voids in the column and such voids can wholly destroy a column's operating characteristics for many separations. Such defects in stainless steel columns are not usually detectable until a standard sample is measured as a control. Indeed, suppliers of quality chromatographic columns, until this day, have pre-tested individually each column before shipment to the customer to assure that the packing is properly placed in the column. Of course, this "certifying procedure" provides no protection against the hazards encountered during shipment or during use by the customer.

A number of solutions have been suggested for holding the packing "in-place". Some of these, like the aforementioned vibration technique and slurrying technique, emphasize a maximum effort to put a conventional packing into the column in such a way as to have it assume a stable position. Other techniques such as those described in U.S. Pat. No. 3,808,125 to Good use rather complex or expensive procedures for fastening the packing to the column wall.

None of these attempts by the prior art have been dependably successful in achieving any of an excellent performance, a column-to-column consistency in separating characteristics, or a desired degree of stability of performance over a period of time for a single column, at a cost which can make the apparatus available to the broadest spectrum of chromatographers.

Although the foregoing description of problems relating to chromatographic columns has been largely devoted to liquid chromatographic columns, it is emphasized that many of the problems described above also relate to gas chromatography, i.e. chromatography wherein the sample and mobile phase are in gaseous, rather than liquid, form. Indeed, in many respects, the problems relate to all packed-bed apparatus comprising a porous mass of particles intended to be intimately and uniformly contacted by a fluid. Such apparatus includes catalytic beds for the treating of gas and liquid, packed beds used in ion exchange processes, in electrophoresis applications, and the like. It is intended that the invention described below be viewed as an improvement in packed-column-preparation for all such processes; albeit, the invention will be seen to have particular advantage in the field of liquid chromatography.

In discussing packed-column processes, it is helpful to recognize four kinds of space, all of which can be referred to as "void volume". These include (1) void volume inside a porous particle; (2) theoretical void volume between particles, i.e. the type of unavoidable volume which would result from a perfectly packed bed of spheres of the same size; (3) void volume which is attributable to imperfect packing of particles, usually present to some extent in any actual system utilizing a particulate-packing system; and (4) void volume which represents relatively large voids resulting from the consolidation of those voids described in (3). Voids (4)

substantially reduce resolution of a sample being subjected to chromatographic analysis.

The invention to be disclosed below is believed to be most useful in avoiding the occurrence of such void volume as described in (4). The present invention also tends to reduce void volume as described in (3); moreover, it makes such void volume more nearly uniform, and closer to a theoretical ideal. Void volume, as generally used herein relates to a composite of void volumes (3) and (4).

Some workers have suggested compression of the packing of a chromatographic column by force directed longitudinally, i.e. parallel to the direction of liquid flow. However, such a procedure is relatively ineffective probably because the packing tends to bridge the column and interfere with propagation of the compression force downwardly throughout the length of the column. An example of such work is described in the Journal of Chromatographic Science of October, 1974, in an article entitled "Description and Performance of an 8 cm i.d. Column For Preparative Scale High Pressure Liquid-Solid Chromatography" by Godbille and Devaux.

The above discussion of the Background of the Invention is made, necessarily, in view of the Applicants' invention to be described below. It should be understood that the collection, interpretation and discussion of this background is not intended to disclose the background from the point of view of one being ordinarily skilled in the art and having no preliminary knowledge of Applicant's invention.

SUMMARY OF THE INVENTION

Therefore, it is an object of the present invention to provide a novel column structure for use in chromatographic applications wherein the column will exhibit improved uniformity of separating characteristics over its product life.

Another object of the invention is to provide a package for shipment of chromatographic packing which package is readily converted into a dependable chromatograhpic column free of any undesirable voids.

Another object of the invention is to provide improved processes for making and operating chromatographic columns.

Still another and broader object of the invention is to provide improved packed columns for use in fluid-contacting processes whatever the chemical nature of the packing or the physical form of the fluid passed therethrough.

Another object of the invention is to provide a novel means for preparing chromatographic columns which provides an improved column-to-column uniformity of separating characteristics.

Still another object of the invention is to provide a column which may tolerate transportation stresses without substantial reduction in the column's eventual performance.

A further object of the invention is to provide a process for making a chromatographic column with such a high degree of reliability that pre-testing of performance characteristics becomes unnecessary.

A further object of the invention is to provide an inexpensive, high-quality chromatographic column which can be a disposable item in many, perhaps most, commercial processing situations.

Another object of the invention is to provide apparatus and process means for reestablishing excellent sample resolution in a chromatographic column after the packing therein has been disturbed.

Another object of the invention is to prepare liquid chromatography apparatus which is easily packed and which can be easily repaired, e.g. by adding new packing or changing the packing.

Still another object of the invention is to provide a column which can be readily "healed" if, somehow, excessive voids appear in the packing as might occur, for example, if packing beads break.

Another object of the invention is the achievement of a column having superior resolution characteristics compared to previously-known columns of like diameter and packing, i.e. a smaller time-concentration profiles of sample components as they emerge from the column.

Other objects of the invention will be obvious to those skilled in the art on reading the objects of this invention.

The above objects have been achieved as a consequence of the discovery that radial compression of the packing within a chromatographic column during the use thereof greatly improves the quality and uniformity of the performance characteristics of the chromatographic column so compressed.

In the most simple case, the column can be filled with packing and compressed just before its use by external pressure acting on the cylindrical wall of the column, e.g. a wall formed of material such as a thin polyethylene, a polytetrafluoroethylene polymer, or like sheet material. The wall is surrounded by a pressure chamber and pressed inwardly about the entire cylindrical bed, thereby compressing the particles slightly and achieving better uniformity throughout the bed. The pressure applied to the bed, preferably should not exceed the lateral, radial, yield point of any portion of the bed, should not cause substantial breaking of particles, and should not exceed the pressure at which the mechanical stability of the wall is maintained. If this happens, there will tend to be a distortion in the uniformity of the cross-sectional size or shape of the bed which is, generally, undesirable and tends to make the desired consistency of the properties of the bed more difficult to achieve. Usually, excellent results can be obtained well below this yield point and the determination thereof is only of academic interest. The yield point, in some case, might result from breaking or gross displacement of particles.

As will be indicated below, it is often preferred to pre-pressurize some of the column packages before they are shipped. This guarantees a predictable uniformity of the commercial product. It is emphasized that such pre-pressurizing, or the filling of a pre-expanded column structure, is not necessary to the practice of this invention.

There are a number of alternate ways the radial pressure can be applied: It can be applied by use of mechanical as well as fluid means. It can be applied from the interior of the column as well as the exterior of the column. Pressure from the exterior of the column is believed to be more desirable because it does not increase the complexity of construction of the column. However, since one of the substantial advantages of the invention is the improved performance and consistency of relatively large diameter columns used in preparative (as opposed to merely analytical) work internal radial compression is sometimes desirable to maximize the distribution of vectors contributing to the radial compression for particulate packing materials. This is believed to be especially so in columns of up to a foot, or even 10 feet, in diameter. (If gas is used as a pressurizing medium, consideration should be given to the permeability of the wall material to the gas being used. Coatings of less gas permeable materials may be indicated in some circumstances.)

In this connection, it can be noted that in most particulate systems any force imposed upon one site will, at some distance from the site, be attenuated to a relatively small and ineffectual force. This invention, in its most advantageous mode, will have every part of the column packing within the aforesaid distance (which may be called a "radius of fluidity") from the portion of the column wherein a force-manifesting strain is imposed.

As indicated above, the pressure applied to a given column should be below the radial yield point of the particular packing mass utilized. The yield point itself will depend on such factors as (1) the nature of the packing and (2) the way the column is packed. Thus, a column which has been packed using a special procedure such as slurry or other techniques adapted to achieve a more densely-packed column, will often be able to withstand a somewhat higher pressure than will a column containing the same column packing which has been compacted to a lesser degree. Nevertheless, in many circumstances, the above considerations become moot, because there simply is no reason to use the more expensive column-filling techniques when the column is to be operated in such a way as to achieve the processing benefits achieved by practice of the process of the invention. A light tapping technique is entirely suitable for filling columns to be operated according to the invention.

In general, satisfactory exterior pressures also depend upon the ease of deformability of the wall, i.e. the force required to push the wall inwardly towards the particles. In a column of 2.25-inch inside diameter and about one foot in length, the following pressure differentials were found to be useful.

| Wall Material | External Jacket Pressure less Internal Column Pressure |
| --- | --- |
| low density polyethylene 0.006-inch wall | about 75 psig |
| polytetrafluoroethylene 0.030-inch wall | about 200 psig |

These parameters were measured in tests wherein the interior operating pressures of the chromatographic columns ranged from 50 to about 500 psig in this series of experiments.

The invention is a much improved way to avoid packing bed voids. The invention is also believed to be an excellent way of reducing, indeed virtually overcoming, wall channeling effects whereby liquid preferentially flows through space at the interface of the column wall and the packing. This is particularly true when a distensible wall (such as organic resin walls formed of polyethylene or halogenated hydrocarbon polymers such as that sold under the trade designation "Teflon" by E. I. duPont DeNemours) is utilized. Notwithstanding the special advantage achievable by reducing wall channeling, the "radial-compression" process described herein allows a column to be repressurized time and again to what is substantially the same condition throughout its volume. The result of this is that a column produced and operated according to the invention is more dependable for a series of comparative experiments than any comparable liquid chromatographic columns known to the art. However, this effect is of major importance even if the column is used only once, because its packing characteristics will be much more dependable when the column is subject to radial compression. Indeed, in columns of larger diameter, e.g. those of over about one inch in diameter, the primary improvements are largely due to the uniform packing achieved by the radial compression. For a given particle size, the undesirable effect of wall channeling in such large columns has been, usually, small in comparison to other imperfections in the packing arrangement.

Distensible polymers include elastomers and rubbers of various types. However, it is important to remember that a chemically inert surface is required for most chemical operations (and especially for liquid chromatographic analysis). Consequently polyolefins and halogenated hydrocarbon polymers like Teflon are preferred. Another highly desirable characteristic of the distensible polymer is a "memory" characteristic well-known to the art and possessed by many plastics like polyethylene and Teflon. This characteristic might be more aptly expressed, in the present situation, as an ability to "forget" the shape assumed during a first pressurization against the packing material and an ability to assume a new shape if later pressed and molded against the packing material after it has been disturbed by movement and shifted relative to the polymeric wall surface.

Another aspect of the present invention is the fact that high performance liquid chromatography columns, even those of the type used in high-pressure liquid chromatography (HPLC) can now be manufactured in a large variety of configurations. The best-known prior art techniques of column-filling utilized special-frequency vibrations or settling of particles from a slurry pumped through the tube. Each of these techniques was basically a settling technique utilizing gravitational force and best-suited for use with an elongate cylinder. The present invention can be used in any configuration including tubes, coils, U-shapes or the like. However, it should be realized that, in many such configurations, the present invention will merely minimize the effect of inherent disadvantages caused by such disadvantages as the lack of equidistant fluid paths through the configuration. These shapes can be oriented vertically or horizontally, the only limitation being that they be so shaped that each segment thereof may be subjected to force vectors generally directed from the outer walls thereof towards the center of the configuration—a condition described as "radial compression" in this application.

Another means for obtaining the desirable radial compression is to form a rigid column, say a steel tube, which has a coating of a deformable material, say a coating of a plastic such as poly (tetrafluoroethylene), polyethylene, or the like on inside thereof. The coating is preferably chemically inert and among current commercial materials, poly (tetrafluoroethylene) is a preferred coating. The coated tube is expanded, e.g. by heat or pressure or both, filled with a packing material and then allowed to contract. This contraction results in a radial compression of the packing particles, with the steel wall acting as a diaphragm. The particles are pushed into the plastic coating to the extent that wall-channeling is virtually eliminated. Residual compression is sufficient to achieve the uniformity of packing compaction that has been described for the externally-applied pressure aspect of this invention.

There is some advantage to use of a prestressed column wherein the chamber wall structure is formed of a relatively non-flexible material like steel. Such a column avoids any marked gradient in differential pressure between the entrance of a column and the exterior of a column. Thus, at higher column operating pressures, there can be no tendency for a packing to be moved from the bottom of the column (where a relatively high pressure differential would be experienced using a flimsy, otherwise non-structured, retaining package) towards the top of the column (where the high internal pressure in the column itself would be much closer to the pressure exerted on the exterior of a relatively flimsy, otherwise non-structured, retaining package).

Also, the prestressed columns have advantage in many low pressure operations wherein the particles are soft, or spongy, or have internal porosity which must be prestressed and, consequently, where very close control of the strain on the particles must be exerted all along the length of the column.

As may be deduced from the above, in larger diameter columns, where wall channeling is not a substantial factor, the above-described pre-compressed metal columns can be used advantageously without a distensible material adapted for conforming to the surface of the packing particles in response to the opposing force exerted by the particles on the surface. This distension reduces the void volume at the interface of said mass of particles with the metal wall of column. "Distensible" in the sense used here means ability to conform to the irregularities of diverse particles in the surface of the mass of packing and to substantially reduce the channeling volume between the packing and the wall.

It is also possible to expand polymeric columns, fill them with packing, and allow them to contract to exert the proper radial pressure on the packing without the need of maintaining an external pressure. However, it is believed that this procedure is best avoided because of the unpredictable nature of conditions to be encountered in transportation of such columns. Nevertheless, it should be noted that such columns can be prepared. Indeed, a small amount of expansion is also advantageously utilized before packing thin-wall plastic columns, but this is done to eliminate ripples and bulges in the compressed wall, a cosmetic advantage to facilitate the filling operations and assure a proper initial packing procedure rather than permanently prestress a diaphragm wall.

It has been found that those advantages of the instant invention relating to (a) reduction or elimination of wall channeling and (b) a more uniform packing also allow optimization of the effects of flow-distributing techniques at the head of a column. That is, the flow-distributing techniques known to the prior art tend to work better when utilized in columns constructed and operated according to the instant invention. Moreover, the instant invention makes the further optimization of flow-distribution apparatus practical and desirable because the packed column is, in many cases, no longer the limiting factor in achieving good uniform flow distribution.

"Bridging" is a phenomena wherein packing arranges itself in such a mechanical relationship with the walls of a column that an arch-like resistance is formed to compression of the packing in directions generally parallel to the walls.

One of the advantages of the instant invention is to avoid bridging interference resistance to effective compression of the columns. However, it should be realized, that by radial compression, it is also possible to effect an improved bridging phenomena wherein vertical increments of packing are isolated by bridges which are relatively close to another. As the bridges become very close to one another, an improved chromatographic column is produced which can be successfully operated at higher pressures than a column containing the same packing which has been operated with prior art techniques. This is so because each bridge protects those particles below it from the pressure exerted above that bridge.

The most advantageous use of this increased bridge frequency is in using relatively soft compressible packing materials such as a relatively large-pore, lightly-crosslinked polymeric packing material sold under the trade designation Suffodex. Advantage is also achieved with somewhat smaller-pore, more crosslinked materials sold under the same trade designation. Such materials are very well known in the art. Somewhat less advantage is achieved with less compressible materials, and the increased bridging is not believed to make a major contribution to the improved performance of alumina and silica-type packing materials; the improved performance of such packing materials in the practice of the instant invention is believed to be primarily due to factors discussed elsewhere in this disclosure.

When gas is used to pressurize the column, it may be desirable to use a wall-material which has a gas-impermeable barrier layer. Various polymeric coating materials are known to be particularly resistant to passage of particular gases and may be used. Also, thin metallic foils may be incorporated between or used in conjunction with or in place of polymeric films to form suitable column wall structures.

ILLUSTRATIVE EXAMPLES OF THE INVENTION

In this application and accompanying drawings, there is shown and described a preferred embodiment of the invention and suggested various alternatives and modifications thereof, but it is to be understood that these are not intended to be exhaustive and that other changes and modifications can be made within the scope of the invention. These suggestions herein are selected and included for purposes of illustration in order that others skilled in the art will more fully understand the invention and the principles thereof and will be able to modify it and embody it in a variety of forms, each as may be best suited in the condition of a particular case.

FIGS. one through nine are sections of a column illustrating steps used to form an externally pressurized column, and the novel compression columns formed by said steps.

FIGS. 10–13 illustrate schematically those steps used to form a column having an exterior compression cylinder lined with a deformable polymeric coating according to the invention and the novel compression column formed by said steps.

Figure 14B:
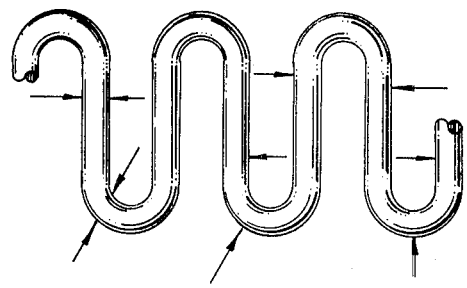
Figure 14A:
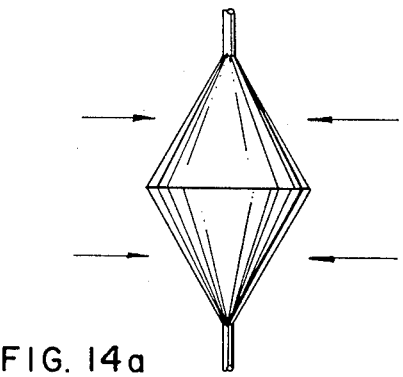

FIGS. 14a and 14b illustrate schematically various configurations of chromatographic tubes which can be advantageously filled according to the invention: These are set out to illustrate one novel aspect of column construction made possible by practice of the invention, i.e. the construction of packed beds which are suitably packed although shaped with conical (FIG. 14a) sinusoidal (FIG. 14b), or other elongate passages which are not reliably packed using the packing techniques of the prior art.

Figure 15:
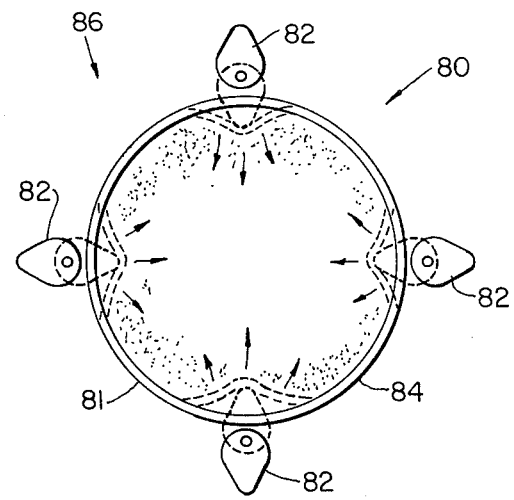

FIG. 15 is a schematic showing the cross section of a cylindrical column about which are mounted mechanically actuated compressing means.

FIG. 1 illustrates a polytetrafluoroethylene tubing 30 of about 0.030 inch wall thickness, 12 inches long and about 2 inches in tubing diameter. FIG. 2 illustrates the placement of the tube in a packing chamber 32. FIG. 3 shows a porous glass-frit plug 38 inserted into the bottom end of the tube to hold it snugly in the packing chamber. A plug 34 is inserted in the top. Gas is admitted into the tube through conduit 36 and plug 34 to obtain an expansion thereof as seen in FIG. 4. Air pressure is used to achieve an expansion of about 15% in volume.

Plug 34 is removed. Then the tube is filled with a chromatographic packing material, 60–200 mesh silica-based packing. Only a slight tapping or shaking action need be used in filling the column. A glass frit 38 is inserted at the top of the column and end caps 39 are bolted on to form a pressure chamber.

FIG. 7 illustrates the radial compression as gas at 250 psig is admitted into chamber 32 through valve 40 to achieve an initial radial compression of the tube. End caps 42 are snapped over the column after it is removed from the packing chamber 32, for protection of the column during shipment.

The column is then ready for shipment. When received, end caps are removed, and it is placed into a pressure vessel such as 50. Gasketed end plates 51 are bolted down with bolts 52, and in general such good practice as is known in the art is followed in manufacture and use of such pressure vessels. In use, the tube is externally pressurized to about 200 psig above the operating pressure of a liquid chromatographic process as measured at the head of the column.

The same procedure is repeated using a medium density polyethylene film. The film was heated to about 110° C. to facilitate its pre-fill expansion to 15%. Such heating resulted in a snug, superior fit of the film over the packing when after compression the film was cooled and allowed to shrink to form a taut package. Indeed, the fit would allow the column to be utilized advantageous at low pressures, say below about 100 psi. However, the column tends to "loosen up" a bit on storage and repressurization is required for the illustrated construction.

FIG. 10 illustrates a steel tube 60 (316 stainless steel) of a wall thickness of 0.080 inch and an inside diameter $d_1$ of about 0.25 inch. The tube is placed in a heat exchanger schematically shown at 61 and heated from 25° C. to 85° C. Simultaneously a slurry of 10-micron silica-based chromatography packing is run through the column in order to deposit the packing according to the well-known slurry techniques. The combination of the pressurized slurry and the heated tube expands the tube during the filling operation substantially to a diameter $d_2$ as seen in FIG. 11.

When the tube is allowed to return to room temperature as seen in FIG. 12, it radially compresses the packing according to the invention. If a wall channel effect is to be avoided or minimized, it is most desirable to utilize a metal tube 62 a wall 64 is coated with about 0.001 inch of a polytetrafluoroethylene polymer 66 which is distensible under the radial compression to conform substantially to the shape of the packing material 69 at interface 68, thereby avoiding highly undesirable wall channeling.

The columns described in FIG. 10–13 are fitted with and include end fittings, as are other columns sold in the chromatographic art, and are shipped pre-compressed for direct use. Their radial compression is permanent: they do not usually require any further compression steps as long as the same packing remains in the column.

A number of simple mechanical means can be used to achieve the required radial compression. These are advantageously constructed so that they reduce the cross-section of the column all the way along its length, i.e. inlet end fitting to outlet fitting. The shrinking of a heat expanded tube is a species of such mechanical means wherein the tube itself is the radial compressing means. In other embodiments of the invention, flexible wall tubes formed of foil, plastic film, or the like are distorted, as from a circular to non-circular cross section, by an external means such as a cam or like device which is forced against the wall to change its shape in such a way as to reduce its cross-sectional area. A decrease in cross-sectional area, typically as little as a 2 to 5% change, is effective in well-packed columns, decreases of over about 10% are seldom required.

FIG. 15 is illustrative of a column equipped with such mechanical pressurizing means. Column 80 comprises a tube formed of 0.030-mil thick polytetrafluoroethylene. It is mounted with 4 cams 82 mounted thereabout in a normal position indicated in solid lines where they do not press into the wall 84. These cams extend along the entire length of flexible column wall 81. When it is desired to apply radial compression, the cams are turned to the position defined by the dotted lines and they so compress packing 86 that the desired amount of radial compression is achieved. As in other aspects of the invention, a distensible polymer surface is advantageous at the interface between column wall and packing.

It is no part of this invention to discuss in detail those well-known aspects of the mechanical arts which can be utilized in devising various means to assure proper compression. Those skilled in the art will be able to devise many such quick-actuating devices capable of performing according to the teachings of this invention. In general, however, it is desirable to have at least two or three different pressure sites on a given column; although in shorter columns, one pressure site can be very effective.

FIG. 15 is also illustrative of the broad scope radial compression is intended to have. Obviously the vectors emanating from the pressure points caused by the cam are not strictly radial nonetheless, they have a substantial, effective, net effect which is radial and act well within the term "radial compression" as it is used in this specification.

There are numerous other means to provide for a source of strain-inducing pressure on the packed bed. For example, the bed could be surrounded by a jacket into which a low-melting alloy such as Woods Metal could be poured, pressurized, and allowed to cool and solidify under pressure. Metals which expand on cooling are preferred. Whenever, repressurization is required to heal, or repack, or repair the packing, the alloy could be melted and repressurized and once again frozen.

Another approach would be to wind a helical wire or tubing or series of circular rings about the column and use thermal or pneumatic or mechanical means to change the dimensions of the tubing or rings and produce a strain, that is a reduction of cross-sectional area on the column.

As has been indicated above, an improved flow distribution is achieved whenever a good flow distribution means is employed at the column inlet, and this distribution is maintained with remarkable fidelity throughout the length of a novel radially compressed column of the type disclosed.

It has been found that it is usually most desirable to apply the strain to a packed column before the column is wetted, ie before the liquid chromatographic procedure is started. When the prepacked columns such as those formed of polymeric walls are to be used, they will often have "refluxed" somewhat over a period of time after the initial packing. Thus, if they are advantageously repressurized before being wetted, the resulting force is maintained on the column during use.

The term "diaphragm" as used herein means a column wall section that can be moved to impart strain to the packing within the column. Many complex structures can be used to achieve this result. As will be suggested by example below, all of the column wall need not be moved, it is often sufficient to impart strain along a single linear situs along the column wall. Also, it is possible to exert such strain by pushing on a substantial number of sites distributed over the column surface. Walls using all such techniques are "diaphragms" according to this general use of the term in this disclosure. Such walls may be internal, e.g. in the center of the column and adapted for movement towards the exterior wall of the column. Nevertheless, it is usually desirable to use one of the relatively simple structures disclosed herein.

There are other ways to place the packing under a suitable, repetitive compressing force. One, is to make a dynamically balanced column spun at high speed about its axis pushing the packing particles outwardly toward the outer wall of the column. It might well be necessary to have an axially-positioned follower device (mechanical or hydraulic) which would expand to the extent necessary to fill any space that outwardly-moving particles left. It is the applicants position that such a device is a mechanical equivalent to the present invention because it would use radial compression and a reduction in effective cross-sectional area of the packing. The primary forces would be outwardly directed in this situation, but the centrifugal device would only be a means for achieving the radial compression. In such a situation, the one operation achievement of compression and taking-up of void volume created by the compression is not achieved, and it is necessary to use the axial follower to take up the void volume. The follower would be means made necessary to avoid a central void from forming, by movement of packing towards the outer wall of the column.

Moreover, a doughnut-shaped column, i.e. one with a hollow axial bore, could be constructed. Not only could pressure be exerted from both internal and external cylindrical walls, but the walls could be used to improve heat transfer properties of the apparatus.

In general, the term "radial compression" is meant to describe a compression wherein the compression forces are predominantly aligned in a direction which is normal to flow of liquid through the column, i.e. in the classical situation of a cylindrical column, the forces would be directed toward the center of the cylinder.

It is to be understood that the following claims are intended to cover all of the generic and specific features of the invention herein described and all statements of the scope of the invention which might be said to fall therebetween.

What is claimed is:

1. In a package of the type defining an elongate chamber holding, and substantially filled by, a porous mass of a stationary-phase, liquid chromatographic, packing material forming means to intimately contact a liquid as it passes through said chamber, and retaining means, at an inlet to and outlet from said chamber for holding said porous mass in said chamber, the improvement wherein said chamber has a flexible wall forming a movable diaphragm means to radially compress said porous mass of packing throughout the cross section of said bed.

2. A package as defined in claim 1 wherein said diaphragm is in a sufficiently snug radially compressing relationship with said porous mass to deform and reduce the void volume between said diaphragm and said mass without further application of external pressure to said diaphragm.

3. A package as defined in claim 1 wherein said mass comprises a stationary-phase, particulate liquid-chromatography packing material.

4. A package as defined in claim 3 wherein said diaphragm comprises an interior wall formed of a distensible organic polymer material said polymer material forming means to press radially against said mass and to conform to the surface of said mass and reduce void volume at the interface of said mass of particles with said diaphragm.

5. A package as defined in claim 4 wherein said diaphragm wall is formed of poly (tetrafluoroethylene).

6. A package as defined in claim 4 wherein said diaphragm wall is formed of polyethylene.

7. A package as defined in claim 1 wherein said diaphragm is so constructed that it forms means to radially compress said mass when an external pressure of about 10 to 1000 psi above the pressure within the chamber is applied to said diaphragm.

8. A package as defined in claim 4 wherein said diaphragm is formed of a polymer of from 0.001 to 0.100 inches in thickness.

9. A package as defined in claim 1 wherein said diaphragm is formed of an organic plastic having sufficiently high memory to be able to at least partially recover its surface shape after pressurization is relieved and forming means to assume a newly-shaped interface, on each pressurization of said diaphragm against said packing, minimizing liquid flow between said diaphragm and packing.

10. A package as defined in claim 8 wherein said diaphragm is formed of polyethylene or polytetrafluoroethylene.

11. A package as defined in claim 9 wherein said mass comprises a stationary-phase, particulate liquid chromatography material.

12. A package as defined in claim 8 wherein said mass comprises a stationary-phase, liquid chromatography material.

13. A package as defined in claim 2 wherein said mass comprises a stationary-phase, particulate liquid chromatography material.

14. A package as defined in claim 10 wherein said mass comprises a stationary-phase, liquid chromatography material.

15. A package as defined in claim 1 wherein said diaphragm comprises a thin layer of metallic foil.

16. A package as defined in claim 15 wherein said diaphragm is so constructed that it forms means to radially compress said mass when an external pressure of about 10 to 1000 psi above the pressure in the chamber, is applied to said diaphragm.

17. A package as defined in claim 15 wherein said mass comprises a stationary-phase, liquid chromatography material.

18. A package as defined in claim 8 wherein said package has a diameter of less than about six inches.

19. A package as defined in claim 3 wherein the chamber is helical in shape.

20. A package as defined in claim 8 wherein the chamber is continuous and comprises at least two segments arranged at angles of substantially less than 180°, one to the other.

21. In an apparatus of the type comprising an elongate chamber having an inlet adapted to receive fluid at one end thereof and a port adapted to discharge fluid at the other end thereof, and further comprising a porous mass a stationary phase of liquid chromatographic packing material substantially filling said chamber, said porous mass forming means to intimately contact said fluid as it passes through the chamber, the improvement wherein said chamber wall is a pre-stressed diaphragm forming means to radially compress said porous mass and maintain said mass in a substantially uniform state of compression of packing material throughout said chamber during shipment or use.

22. Apparatus as defined in claim 21 wherein said porous mass is particulate and comprises the immobile phase component of a liquid chromatography packing material.

23. Apparatus as defined in claim 22 wherein said chamber wall is formed of stainless steel.

24. Apparatus as defined in claim 22 wherein said chamber is formed of a metallic material and the wall of said chamber comprises, in contact with said particulate material, a coating of a distensible organic material forming means to conform to the surface of said mass of particles and reduce viod volume at the interface of said mass of particles with said chamber wall.

25. Apparatus as defined in claim 24 wherein said organic material is formed of polytetrafluoroethylene.

26. Apparatus as defined in claim 24 wherein said organic material is formed of polyethylene.

27. Apparatus as defined in claim 2 wherein said package has a diameter of less than about six inches.

28. In a liquid chromatography apparatus of the type comprising a chamber having an inlet adapted to receive liquid at one end thereof and a port adapted to discharge fluid at the other end thereof, and further comprising a porous mass substantially filling said chamber, said mass comprising an immobile phase material forming means to differentially retard the passage of chemical compounds through said chamber the improvement wherein,
(a) said apparatus comprises means to radially compress said particulate mass throughout said chamber, to decrease the cross section thereof with substantial uniformity along the length of said chamber and
(b) means to take up any decrease in volume of said mass caused by said compression.

29. In apparatus as defined in claim 28 wherein, (a) said chamber wall is a diaphragm means which, upon application of an external pressure thereto, forms means to radially compress said mass, and wherein said apparatus comprises (b) means to reduce the cross-sectional area of said chamber, and radially compress said mass.

30. Apparatus as defined in claim 29 wherein said mass is particulate and said diaphragm wall is formed of a distensible organic material forming means to conform to the surface of said particulate mass and to reduce void volume at the interface of said mass with said diaphragm.

31. Apparatus as defined in claim 30 wherein said chamber wall is formed of polyethylene.

32. Apparatus as defined in claim 30 wherein said chamber wall is formed of polytetrafluoroethylene.

33. Apparatus as defined in claim 28 wherein said chamber has a diameter of less than about six inches.

34. Apparatus as defined in claim 30 wherein said chamber has a diameter of less than about six inches.

35. Apparatus as defined in claim 28 wherein, at said inlet port, there is means to distribute liquid entering said chamber evenly across the top of said chamber.

36. Apparatus as defined in claim 30 wherein at said inlet port, there is means to distribute liquid entering said chamber evenly across the top of said chamber.

37. A package as defined in claim 1 wherein said diaphragm means if formed of polyethylene.

38. A package as defined in claim 3 wherein said package has a diameter of less than about six inches.

39. A package as defined in claim 13 wherein said package has a diameter of less than about six inches.

40. Apparatus as defined in claim 3 wherein said movable diaphragm is a means to improve bridging stability of said particles and to increase stability of the particulate mass.

41. Apparatus as defined in claim 34 wherein said diaphragm forms means to improve bridging stability of said particles and to increase the stability of said mass.

* * * * *

UNITED STATES PATENT AND TRADEMARK OFFICE
CERTIFICATE OF CORRECTION

PATENT NO. : 4,250,035
DATED : February 10, 1981
INVENTOR(S) : Patrick D. McDonald et al.

It is certified that error appears in the above-identified patent and that said Letters Patent are hereby corrected as shown below:

Column 2, line 6 "Each" should be --Even--;

Column 4, line 14 "i.e." should be --e.g.--;

Column 10, line 55 after "radial" insert --;--;

Column 11, line 18 "refluxed" should be --relaxed--;

Column 13, line 16 "3" should be --1--;

Column 13, line 46 "viod" should be --void--; and

Column 14, line 43 "if" should be --is--.

Signed and Sealed this

Fourteenth Day of July 1981

[SEAL]

Attest:

Attesting Officer

GERALD J. MOSSINGHOFF

Commissioner of Patents and Trademarks